(12) United States Patent
Ahmed et al.

(10) Patent No.: US 11,840,547 B1
(45) Date of Patent: Dec. 12, 2023

(54) NANO-SIZED 4-BROMO-2-[(9H-PURIN-6-YLIMINO)-METHYL]-PHENOL IMINE PD(II) COMPLEX FOR SUPERIOR PHARMACEUTICAL APPLICATIONS

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Mohamed Abdel-Hammed Abdel-Aziz, Al-Ahsa (SA); Ahmed M. Abu-Dief, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/228,238

(22) Filed: Jul. 31, 2023

(51) Int. Cl.
*A61P 35/00* (2006.01)
*C07F 15/00* (2006.01)
*A61P 31/10* (2006.01)
*A61P 31/04* (2006.01)

(52) U.S. Cl.
CPC .......... *C07F 15/0066* (2013.01); *A61P 31/04* (2018.01); *A61P 31/10* (2018.01); *A61P 35/00* (2018.01)

(58) Field of Classification Search
CPC ...... C07F 15/0066; A61P 31/04; A61P 31/10; A61P 35/00
USPC ........................................................ 514/186
See application file for complete search history.

(56) References Cited

FOREIGN PATENT DOCUMENTS

| CN | 113501822 B | 3/2023 |
| KR | 102520084 B1 | 4/2023 |

OTHER PUBLICATIONS

Abu-Dief et al., Chemistry Department, College of Science, Taibah University, "Fabrication, structural elucidation, theoretical, TD-DFT, vibrational calculation and molecular docking studies of some novel adenine imine chelates for biomedical applications", Journal of Molecular Liquids, vol. 365, Nov. 1, 2022.

Rehman et al., Department of Biochemistry and Molecular Biology, School of Basic Medical Sciences, Capital Medical University, "Synthesis, characterization, antimicrobial and antitumor screening of some diorganotin(IV) complexes of 2-[(9H-Purin-6-ylimino)]-phenol", European Journal of Medicinal Chemistry, vol. 44, Issue 10, Oct. 2009, pp. 3981-3985.

*Primary Examiner* — Taylor V Oh
(74) *Attorney, Agent, or Firm* — Nath, Goldberg & Meyer; Richard C. Litman

(57) ABSTRACT

A novel nano-sized 4-Bromo-2-[(9H-purin-6-ylimino)-methyl]-phenol imine Pd(II) complex, its synthesis, and its use for potential super pharmaceutical applications.

15 Claims, 1 Drawing Sheet

NANO-SIZED 4-BROMO-2-[(9H-PURIN-6-YLIMINO)-METHYL]-PHENOL IMINE PD(II) COMPLEX FOR SUPERIOR PHARMACEUTICAL APPLICATIONS

BACKGROUND

1. FIELD

The present disclosure relates to a novel nano-sized 4-Bromo-2-[(9H-purin-6-ylimino)-methyl]-phenol imine Pd(II) complex, its synthesis, and its use for potential superior pharmaceutical applications.

2. DESCRIPTION OF THE RELATED ART

Over recent decades, supramolecular chemistry has become a matter of interest. The design and development of new biomaterials and molecular frameworks have increased rapidly, addressing the coordination chemistry of biologically active chelates.

Adenine is one of the two purine nucleobases (the other being guanine) used in forming nucleotides of nucleic acids. In DNA, adenine (A) binds to thymine (T) via two hydrogen bonds to assist in stabilizing the nucleic acid structures. In RNA, which is used for protein synthesis, adenine (A) binds to uracil (U).

On the other hand, cancer is killing millions of people worldwide, and the design of small molecules (metal-based drugs) that bind and react at specific sequences with CT-DNA (cell-free or circulating tumour DNA) is especially important in the development of new therapeutic reagents. Adenine is one of the most interesting biological ligands used for preparing and synthesizing different types of complexes.

Adenine Schiff bases have demonstrated beneficial pharmacological characteristics such as antimicrobial, pesticide, fungicidal, and insecticidal activities. The 1st row of transition metal chelates has numerous uses in various domains. Due to their advantages, adenine Schiff bases play an important role in chemistry and are a targeted molecule for many synthetic chemists.

Thus, new adenine-based molecules solving the aforementioned problems are desired.

SUMMARY

The present subject matter relates to a novel nano-sized 4-Bromo-2-[(9H-purin-6-ylimino)-methyl]-phenol imine Pd(II) complex, its synthesis, and its use for potential superior pharmaceutical applications.

In an embodiment, the present subject matter relates to a 4-Bromo-2-[(9H-purin-6-ylimino)-methyl]-phenol imine Pd(II) complex having the formula I:

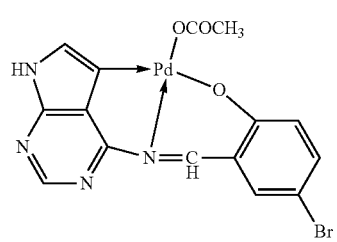

I

In another embodiment, the present subject matter relates to a pharmaceutically acceptable composition comprising a therapeutically effective amount of the 4-Bromo-2-[(9H-purin-6-ylimino)-methyl]-phenol imine Pd(II) complex as described herein and a pharmaceutically acceptable carrier.

In a further embodiment, the present subject matter relates to a method of treating a cancer in a patient, comprising administering to a patient in need thereof a therapeutically effective amount of the 4-Bromo-2-[(9H-purin-6-ylimino)-methyl]-phenol imine Pd(II) complex as described herein.

In an embodiment, the present subject matter relates to a method of treating a microbial infection in a patient, comprising administering to a patient in need thereof a therapeutically effective amount of the 4-Bromo-2-[(9H-purin-6-ylimino)-methyl]-phenol imine Pd(II) complex as described herein.

In another embodiment, the present subject matter relates to a method of promoting an antioxidant effect in a patient, comprising administering to a patient in need thereof a therapeutically effective amount of the 4-Bromo-2-[(9H-purin-6-ylimino)-methyl]-phenol imine Pd(II) complex as described herein.

In a further embodiment, the present subject matter relates to a method of making the 4-Bromo-2-[(9H-purin-6-ylimino)-methyl]-phenol imine Pd(II) complex as described herein, the method comprising: adding a solution of Pd(acetate)2 in acetone to a mixture of 4-Bromo-2-[(9H-purin-6-ylimino)-methyl]-phenol imine ligand in acetone to obtain a first mixture; sonicating the first mixture; and obtaining the 4-Bromo-2-[(9H-purin-6-ylimino)-methyl]-phenol imine.

These and other features of the present subject matter will become readily apparent upon further review of the following specification.

DETAILED DESCRIPTION OF THE PREFERRED EMBODIMENTS

Figure 1:
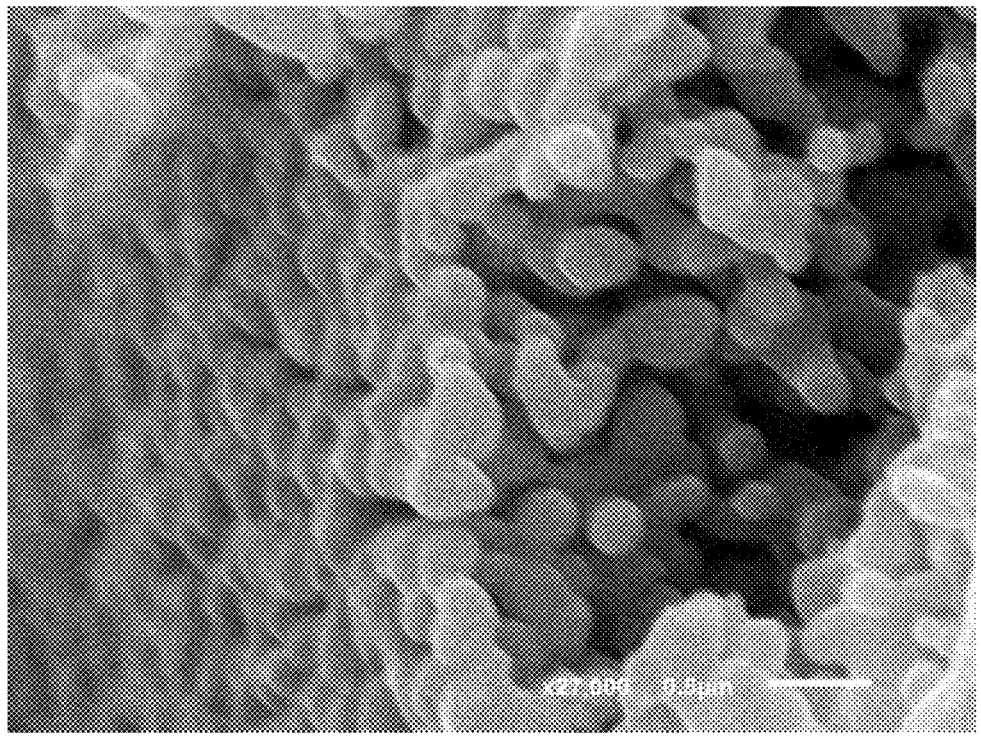
FIG. 1 shows a SEM image of the 4-Bromo-2-[(9H-purin-6-ylimino)-methyl]-phenol imine Pd complex.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a 4-Bromo-2-[(9H-purin-6-ylimino)-methyl]-phenol imine complex having the formula I:

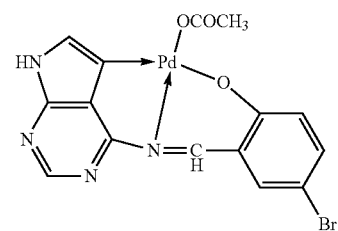

In certain embodiments, the complex can be formed as nanoparticles. In other embodiments, the nanoparticles can have a semi-spherical shape. In further embodiments, the nanoparticles can have an average size of about 20 nm to about 25 nm, about 20 nm, about 21 nm, about 22 nm, about 23 nm, about 24 nm, about 25 nm, or about 22 nm. Since the present complex is itself nanosized, it does not need to be loaded onto other particles to increase its activity. Further, in an embodiment, the size of the complex directly, favorably affects its uses for super pharmaceutical applications.

In another embodiment, the present subject matter relates to a pharmaceutically acceptable composition comprising a therapeutically effective amount of the 4-Bromo-2-[(9H-purin-6-ylimino)-methyl]-phenol imine Pd(II) complex as described herein and a pharmaceutically acceptable carrier.

In an embodiment, the pharmaceutical composition can be formulated as an oral dosage form.

In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

The present compounds may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

The present compounds have valuable pharmaceutical properties, which make them commercially utilizable. Accordingly, the present subject matter further relates to use of the present compounds for the treatment of diseases such as cancers.

Accordingly, in a further embodiment, the present subject matter relates to a method of treating a cancer in a patient, comprising administering to a patient in need thereof a therapeutically effective amount of the 4-Bromo-2-[(9H-purin-6-ylimino)-methyl]-phenol imine Pd(II) complex as described herein.

In an embodiment, the cancer is breast cancer.

In another embodiment of the present subject matter, the present complex demonstrated in vitro anticancer action against a human breast cancer cell line. Accordingly, the present subject matter relates to methods of treating a cancer in a patient by administering the complex presented herein to a patient in need thereof.

In one embodiment, a present complex engaged for in vitro study against a breast cancer cell line can display an $IC_{50}$ concentration of 2.2 µg/ml.

In a further embodiment, the present subject matter relates to a method of treating a microbial infection in a patient, comprising administering to a patient in need thereof a therapeutically effective amount of the 4-Bromo-2-[(9H-purin-6-ylimino)-methyl]-phenol imine Pd(II) complex as described herein.

In an embodiment, the microbial infection is caused by one or more of *E. coli*, and *Aspergillus flavus*.

In an embodiment, a present complex engaged for in vitro study against *E. coli* can display an inhibition zone of about 40 mm and an MIC of about 1.0 µg/ml.

In a further embodiment, a present complex engaged for in vitro study against *Aspergillus flavus* can display an inhibition zone of about 30 mm and an MIC of about 1.50 µg/ml.

In another embodiment, the present subject matter relates to a method of promoting an antioxidant effect in a patient, comprising administering to a patient in need thereof a therapeutically effective amount of the 4-Bromo-2-[(9H-purin-6-ylimino)-methyl]-phenol imine Pd(II) complex as described herein.

In one embodiment, a present complex engaged for in vitro study against a breast cancer cell line as an antioxidant can display an $IC_{50}$ concentration of 7.5 µg/ml.

The present subject matter further relates to a method of treating or preventing a disease comprising administering to a patient in need thereof a therapeutically effective amount of the complex herein.

In particular, the present subject matter relates to a method of treating one of the above-mentioned diseases or disorders comprising administering to a patient in need thereof a therapeutically effective amount of the complex herein.

In the above methods, the patient is preferably a mammal, more preferably a human. In an embodiment, the present complex can be used in combination therapy with one or more additional active agents.

In a further embodiment, the present subject matter relates to a method of making the 4-Bromo-2-[(9H-purin-6-ylimino)-methyl]-phenol imine Pd(II) complex as described herein, the method comprising: adding a solution of Pd(acetate)$_2$ in acetone to a mixture of 4-Bromo-2-[(9H-purin-6-ylimino)-methyl]-phenol imine ligand in acetone to obtain a first mixture; sonicating the first mixture; and obtaining the 4-Bromo-2-[(9H-purin-6-ylimino)-methyl]-phenol imine.

In an embodiment of the present production methods, the 4-Bromo-2-[(9H-purin-6-ylimino)-methyl]-phenol imine Pd(II) complex can be obtained as a nanosized complex. Further, the 4-Bromo-2-[(9H-purin-6-ylimino)-methyl]-phenol imine Pd(II) complex can be obtained as a dark brown crystalline powder.

In an embodiment, the Pd(acetate)$_2$ and the 4-Bromo-2-[(9H-purin-6-ylimino)-methyl]-phenol imine ligand can be mixed in an about 1:1 molar ratio.

In a further embodiment, the first mixture can be sonicated for at least about 60 minutes.

The following examples relate to various methods of manufacturing certain specific compounds as described herein. All compound numbers expressed herein are with reference to the synthetic pathway figures shown above.

EXAMPLES

Example 1

Preparation of 4-Bromo-2[(9H-purin-6-ylimino)-methyl]-phenol imine Pd(II) complex A solution of Pd(acetate)$_2$ (0.5 mmol, 112.25 mg) in acetone was added stepwise to 4-Bromo-2-[(9H-purin-6-ylimino)-methyl]-phenol imine ligand (318.13 mg, 0.5 mmol) in acetone, and the mixture was sonicated for 60 minutes, then a dark brown crystalline powder of the nano-sized complex was obtained.

Figure 2:
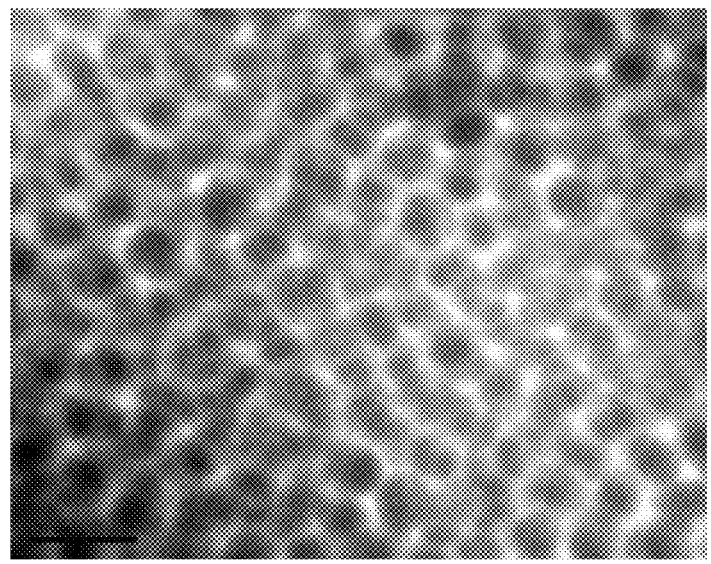
FIG. 2 shows a TEM image of the 4-Bromo-2-[(9H-purin-6-ylimino)-methyl]-phenol imine Pd complex.

Characterization of the prepared nano-complex using SEM and TEM analysis is shown in FIGS. 1 and 2, respectively. The prepared complex is a nanoparticle with a semi-sphere shape. According to the TEM image, the average size of the prepared nano complex is 22 nm. This affects directly on the super pharmaceutical application of the prepared complex.

Example 2

Antimicrobial Activity—*E. coli*

The prepared nano complex showed potent antibacterial activity against *E. coli* bacteria with an inhibition zone of 40 mm and an MIC of 1.00 µg/ml compared with the standard drug Ofloxacin (35 mm and MIC 2.50 µg/ml).

Example 3

Antifungal activity—*Aspergillus flavus*

The prepared complex showed enhanced activity against *Aspergillus flavus* fungi with an inhibition zone of 30 mm and an MIC of 1.50 µg/ml compared with the standard drug Fluconazol (24 mm and MIC 2.00 µg/ml).

Example 4

Anti-Cancer Activity—Breast Cancer

The prepared complex showed super anticancer activity with an $IC_{50}$ of 2.2 µg/ml against a breast cancer cell line compared with the vinblastine standard drug ($IC_{50}$=4.7 µg/ml).

Example 5

Antioxidant Activity

The prepared complex showed super antioxidant activity with an $IC_{50}$ of 7.5 µg/ml against a breast cancer cell line compared with the 1-ascorbic acid standard antioxidant ($IC_{50}$=45.7 µg/ml).

It is to be understood that the 4-Bromo-2-[(9H-purin-6-ylimino)-methyl]-phenol imine Pd(II) complex is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A 4-Bromo-2-[(9H-purin-6-ylimino)-methyl]phenol imine Pd(II) complex having the formula I:

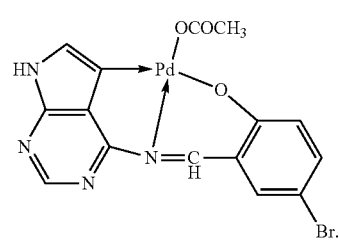

2. The 4-Bromo-2-[(9H-purin-6-ylimino)-methyl]-phenol imine complex of claim 1, wherein the complex is formed as nanoparticles.

3. The 4-Bromo-2-[(9H-purin-6-ylimino)-methyl]phenol imine Pd(II) complex of claim 2, wherein the nanoparticles have a semi-spherical shape.

4. The 4-Bromo-2-[(9H-purin-6-ylimino)-methyl]phenol imine Pd(II) complex of claim 2, wherein the nanoparticles have an average size of 20 nm to 35 nm.

5. The 4-Bromo-2-[(9H-purin-6-ylimino)-methyl]phenol imine Pd(II) complex of claim 4, wherein the nanoparticles have an average particle size of 22 nm.

6. A pharmaceutically acceptable composition comprising a therapeutically effective amount of the 4-Bromo-2-[(9H-purin-6-ylimino)-methyl]phenol imine Pd(II) complex of claim 1 and a pharmaceutically acceptable carrier.

7. The pharmaceutical composition of claim 6, formulated as an oral dosage form.

8. A method of treating a cancer in a patient, comprising administering to a patient in need thereof a therapeutically effective amount of the 4-Bromo-2-[(9H-purin-6-ylimino)-methyl]-phenol imine Pd(II) complex of claim 1, wherein the cancer is breast cancer.

9. A method of treating a microbial infection in a patient, comprising administering to a patient in need thereof a therapeutically effective amount of the 4-Bromo-2-[(9H-purin-6-ylimino)-methyl]-phenol imine Pd(II) complex of claim 1, wherein the microbial infection is caused by one or more of *E. coli* and *Aspergillus flavus*.

10. A method of promoting an antioxidant effect in a patient, comprising administering to a patient in need thereof a therapeutically effective amount of the 4-Bromo-2-[(9H-purin-6-ylimino)-methyl]-phenol imine Pd(II) complex of claim 1.

11. A method of making the 4-Bromo-2-[(9H-purin-6-ylimino)-methyl]phenol imine Pd(II) complex of claim 1, the method comprising:
 adding a solution of Pd(acetate)$_2$ in acetone to a mixture of 4-Bromo-2-[(9H-purin-6-ylimino)-methyl]-phenol imine ligand in acetone to obtain a first mixture;
 sonicating the first mixture; and
 obtaining the 4-Bromo-2-[(9H-purin-6-ylimino)-methyl]phenol imine.

12. The method of claim 11, wherein the 4-Bromo-2-[(9H-purin-6-ylimino)-methyl]-phenol imine Pd(II) complex is obtained as a nanosized complex.

13. The method of claim 11, wherein the 4-Bromo-2-[(9H-purin-6-ylimino)-methyl]-phenol imine Pd(II) complex is obtained as a dark brown crystalline powder.

14. The method of claim 11, wherein the Pd(acetate)$_2$ and the 4-Bromo-2-[(9H-purin-6-ylimino)-methyl]-phenol imine ligand are mixed in a 1:1 molar ratio.

15. The method of claim 11, wherein the first mixture is sonicated for at least 60 minutes.

\* \* \* \* \*

UNITED STATES PATENT AND TRADEMARK OFFICE
CERTIFICATE OF CORRECTION

PATENT NO. : 11,840,547 B1
APPLICATION NO. : 18/228238
DATED : December 12, 2023
INVENTOR(S) : Hany Mohamed Abd El-Lateef Ahmed et al.

Page 1 of 1

It is certified that error appears in the above-identified patent and that said Letters Patent is hereby corrected as shown below:

On the Title Page

Inventors item (72), for Inventors 3-4, please delete and replace with the updated residences as follows:
Mohamed Abdel-Hammed Abdel-Aziz, Sohag (EG); Ahmed M. Abu-Dief, Al-Madina Al-Mounawara (SA)

Signed and Sealed this
Ninth Day of April, 2024

Katherine Kelly Vidal
*Director of the United States Patent and Trademark Office*